Figure 1:
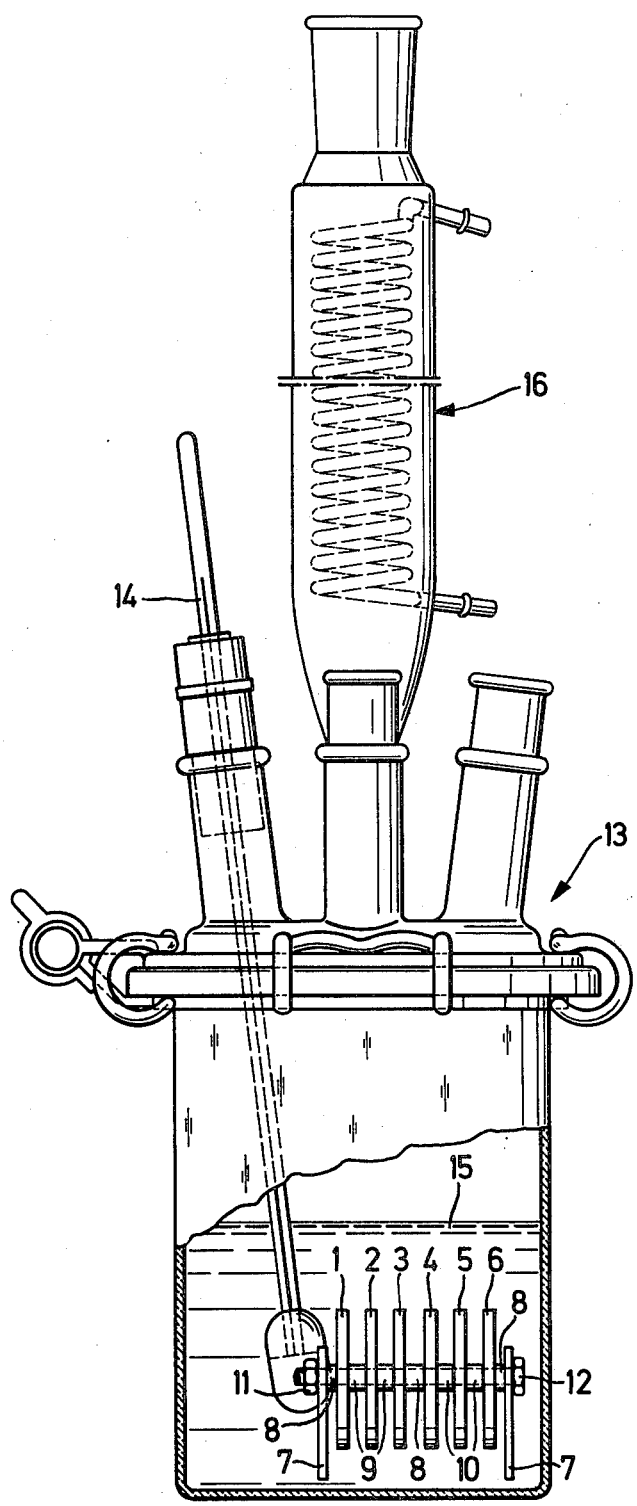

United States Patent [19]

United States Patent [19]

Popplewell, deceased et al.

[11] 4,177,155
[45] Dec. 4, 1979

[54] ADDITIVES FOR WATER-BASED FUNCTIONAL FLUIDS

[75] Inventors: Alan F. Popplewell, deceased, late of Manchester, England, by Margaret R. Popplewell, legal representative; David R. Clark, Sale, England

[73] Assignee: Ciba-Geigy Corporation, Ardsley, N.Y.

[21] Appl. No.: 798,517

[22] Filed: May 19, 1977

Related U.S. Application Data

[63] Continuation-in-part of Ser. No. 649,109, Jan. 14, 1976, abandoned.

[30] Foreign Application Priority Data

Jan. 23, 1975 [GB] United Kingdom ................ 2929/75

[51] Int. Cl.$^2$ ............... C07D 235/08; C07D 249/18; C07D 403/06
[52] U.S. Cl. .................... 252/49.3; 252/77; 544/366; 544/370; 548/328; 548/333
[58] Field of Search .............. 260/268 BC, 308 B; 252/77, 493; 544/366, 370; 548/328, 333

[56] References Cited

U.S. PATENT DOCUMENTS 3,413,227  11/1968  Howard et al. .............. 252/51.5

FOREIGN PATENT DOCUMENTS 1061904  3/1967  United Kingdom ............... 260/308 B

OTHER PUBLICATIONS

Bachman et al., J. Amer. Chem. Soc., vol. 68, pp. 2496-2499 (1946).
Burckhalter et al., J. Amer. Chem. Soc., vol. 74, pp. 3868-3870 (1952).

Primary Examiner—Paul M. Coughlan, Jr.
Attorney, Agent, or Firm—Luther A. R. Hall

[57] ABSTRACT

Selected N-aminomethyl-triazoles and imidazoles are prepared by the Mannich reaction on benzotriazoles or benzimidazoles with formaldehyde and primary or secondary amines. The products consist mainly of the 1-isomers. The compounds are metal passivators and are used as additives for water-based functional fluids being in contact with metals. These compounds with polar substituents on the amino-group are especially useful in water-based fluids such as anti-freeze or metal-working fluids.

24 Claims, 1 Drawing Figure

ADDITIVES FOR WATER-BASED FUNCTIONAL FLUIDS

This is a continuation-in-part application of copending application, Ser. No. 649,109, filed Jan. 14, 1976, now abandoned.

BACKGROUND OF THE INVENTION

The present invention relates to additives for water-based functional fluids.

Benzotriazole and derivatives thereof have been known for many years to be effective metal passivators, especially as copper passivators, for use in a range of substrates. Benzotriazole itself and many of its derivatives have, however, limited application because of their poor solubility.

British Pat. No. 1,061,904 describes benzotriazole derivatives with various non-polar substituents which are useful metal passivators for non-aqueous based systems such as oils, lubricants and some hydraulic fluids.

Certain previously unknown benzotriazole and benzimidazole derivatives having polar substituents combine an improved level of solubility in a wide range of water-based functional fluids along with a high level of metal passivation.

Accordingly, the present invention pertains to such derivatives and to compositions passivated thereby.

DETAILED DISCLOSURE

The benzotriazole and benzimidazole compounds of this invention have the formula

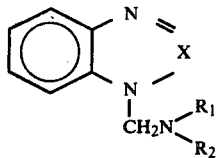

I wherein X is N or CR, R is hydrogen or an alkyl of 1 to 4 carbon atoms, preferably methyl, $R_1$ and $R_2$ are the same or different and each is a residue of the formula $R_3O[(alkylene)O]_x$alkylene, $R_3$ is hydrogen or alkyl of 1 to 2 carbon atoms, preferably hydrogen or methyl, "alkylene" is a straight or branched chain alkylene of 2 to 3 carbon atoms, and x is 0, 1, 2, 3, or 4; or $R_1$ is said residue and $R_2$ is hydrogen, alkyl or 1 to 4 carbon atoms, cyclohexyl, benzyl or a radical of the formula

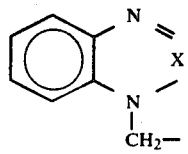

II, or $R_1$ and $R_2$ together are

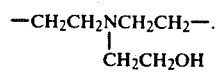

Preferably the compounds of formula I have X as N or CR, R being hydrogen or methyl; $R_1$ and $R_2$ are the same or different and each is a residue of the formula $R_3O[(alkylene)O]_x$alkylene where $R_3$ is hydrogen or methyl and x is 0; or $R_1$ is said residue and $R_2$ is hydrogen, methyl or the radical of the formula

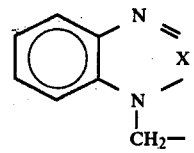

or $R_1$ and $R_2$ together are

Most preferably the compounds of formula I have X as N or CH and still more preferred are the compounds where X is N.

Moreover, it is essential that the substituent ($R_1$ or $R_2$) on the N atom of the compound of formula I constitutes a polar function. It is particularly preferred that each of $R_1$ and $R_2$ is a residue of formula $R_3O[(alkylene)O]_x$-alkylene wherein $R_3$ has its previous significance and $R_3$ is preferably H and x is preferably 0.

However, the most preferred compounds of the present invention are those of formula I wherein $R_1$ and $R_1$ are the same or different and each is $R_3O[(alkylene)O]_x$-(alkylene) or $R_1$ is such a residue and $R_2$ is hydrogen or methyl, $R_3$ is hydrogen or methyl, and x is 0.

Specific examples of compounds in accordance with the present invention are:
1-diethanolaminomethylbenzotriazole
1-diethanolaminomethylbenzimidazole
1-diisopropanolaminomethylbenzotriazole
1-diisopropanolaminomethylbenzimidazole
N,N-bis(1-benzotriazolylmethyl)ethanolamine
N,N-bis(1-benzimidazolylmethyl)-n-propanolamine
N,N-bis(1-benzotriazolylmethyl)-isopropanolamine
1-(N-methyl-ethanolaminomethyl)benzotriazole
N,N-bis(1-benzimidazolylmethyl)-3-amino-3-methyl-butanol
N,N-bis(1-benzimidazolylmethyl)-3-methoxypropylamine
1-(N-methyl-ethanolaminomethyl)-2-methylbenzimidazole
N,N-bis(1-benzotriazolylmethyl)ethoxyethoxypropylamine A process of producing a compound of formula I comprises reacting a compound having the formula:

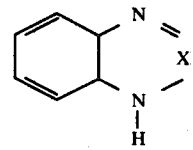

III with formaldehyde and with an amine having the formula:

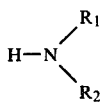

wherein $R_1$ and $R_2$ have their previous significance.

Compounds of formula III which are suitable starting-materials for use in the process of the present invention include benzotriazole and benzimidazole. Preferably, however, compound III is benzotriazole itself.

The formaldehyde reactant is conveniently used in the commercially-available forms, i.e., formalin or paraformaldehyde.

Examples of suitable amine compounds of formula IV are primary amines of formula $R_1NH_2$ wherein $R_1$ has its previous significance, and secondary amines of formula

wherein $R_1$ and $R_2$ have their previous significance.

The relative proportions of the compound of formula III and IV, and formaldehyde can vary according to whether the amine of formula IV is a primary or secondary amine.

When the amine of formula IV is a primary amine, the molar ratio of compound III:formaldehyde:amine IV may be substantially either 2.0:2.0:1.0 or 1.0:1.0:1.0 and when amine IV is a secondary amine the molar ratio of compound III:formaldehyde:amine IV is preferably substantially 1.0:1.0:1.0.

The process of the present invention is conveniently effected by heating all the reactants together at an elevated temperature, for instance a temperature within the range of from 50° to 120° C. If desired, the compound of formula III and formaldehyde may first be reacted together to produce the corresponding N-methylol compound, prior to reaction with the amine of formula IV.

The Mannich base compounds of formula I have been found to combine excellent metal passivation with high solubility in a wide range of water-based functional fluids.

Accordingly, the present invention also provides a composition comprising a water-based functional fluid and as metal passivator, a passivating amount of a compound of formula I as hereinbefore defined.

Preferably, the composition contains from 0.001% to 5% by weight of the compound of formula I based on the total weight of the composition.

Examples of water-based functional fluids useful in the composition of the invention are hydraulic fluids based on aqueous polyglycol/polyglycol ether mixtures, glycol systems, oil-in-water emulsions and water-in-oil emulsions and metal-working fluids having as their base aqueous systems, as well as aqueous glycol anti-freeze compositions.

Of particular interest in this invention, are those functional fluids which have a water base, e.g., aqueous-based anti-freeze, hydraulic and metal-working fluids. For use in this type of water-based functional fluid, the compounds of formula I must bear a polar substituent on the nitrogen atom of the heterocyclic ring.

When the composition of the invention comprises an aqueous-based functional fluid, the substituents $R_1$ and $R_2$ in the compounds of formula I are preferably the same and each is a residue of formula $R_3O[(alkylene)O]_x$-(alkylene) wherein $R_3$ has its previous significance, or $R_3$ is preferably H and x is zero.

Depending on the nature of the water-based functional fluid, the composition of the invention preferably contains one or more co-additives.

Examples of co-additives suitable for use in aqueous based products and/or glycol-glycol ether include anti-oxidants, corrosion and rust-inhibitors, metal passivators, extreme pressure anti-wear additives, biocides, buffering agents and anti-foams.

Examples of antioxidants are: 2,6-ditertiarybutyl-p-cresol and phenyl-α-naphthylamine.

Examples of corrosion and rust inhibitors are: sodium nitrite, sodium benzoate, morpholine, disodium hydrogen phosphate, disodium sebacate, triethanolamine sebacate, triethanolamine phosphate; and amine salts of arylsulphonamidocarboxylic acids.

Examples of metal passivators are: benzotriazole and sodium mercaptobenzothiazole.

Examples of extreme pressure/anti-wear additives are: chlorinated paraffins; sulphurised sperm oil; sulphurised olefins, ethoxylated partial esters and polyglycols.

Examples of buffering agents are: borax and triethanolamine.

Examples of biocides are: 2,4,5-trichlorophenol; sodium salt of 2,2'-dihydroxy-5,5'-di-chlorodiphenylmethane; and sodium salt of orthophenylphenol.

Examples of antiform are silicones.

All the benzotriazole derivatives of this invention were prepared by the same general method described below for making the Mannich bases from secondary amines. When the Mannich base is prepared from a primary amine, half the molar quantity of amine is used.

Where solid products were obtained, recrystallization was usually best effected from ethyl acetate.

The products are essentially 1-N-substituted though there is evidence from proton n.m.r. spectroscopy that some 2-N-substitution has taken place and is present to varying extents (up to 20%) in some benzotriazole products.

In Examples 1-6, the compounds of the instant invention are Mannich bases derived from secondary amines and have the general formula

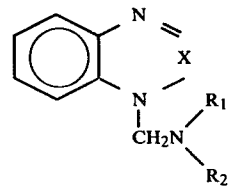

| Example | X | $R_1$ | $R_2$ |
|---------|----|------------------------|------------------------|
| 1 | N  | $-CH_2CH_2OH$          | $-CH_2CH_2OH$          |
| 2 | CH | $-CH_2CH_2OH$          | $-CH_2CH_2OH$          |
| 3 | N  | $-CH_2CH_2OH$          | $-CH_3$                |
| 4 | CH | $-CH_2CH_2OH$          | $-CH_3$                |
| 5 | N  | $-CH_2CHCH_3$<br>$\quad\ \ \ \ OH$ | $-CH_2CHCH_3$<br>$\quad\ \ \ \ OH$ |

-continued

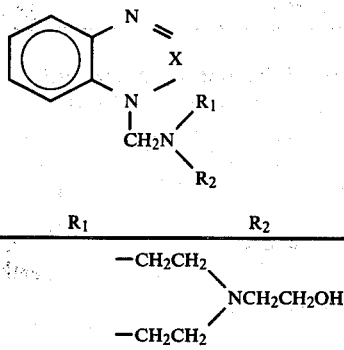

| Example | X | R₁ | R₂ |
|---|---|---|---|
| 6 | N | —CH₂CH₂\NCH₂CH₂OH /—CH₂CH₂ | |

EXAMPLE 1

1-Diethanolaminomethylbenzotriazole 23.82 parts of benzotriazole and 21.03 parts of diethanolamine were mixed with 75 parts of ethanol and 6.0 parts of formaldehyde was then added as a 36% aqueous solution. The mixture was heated to boiling and reflux conditions maintained for 8 hours (higher mol. wt. amines required a reaction time of up to 16 hours to effect satisfactory yields). After cooling, the solvent was removed under water pump vacuum and the remaining product azeotroped with 3×50 parts of ethanol also under water pump vacuum. In this way, 1-diethanolaminomethylbenzotriazole was obtainedd in 80% yield as a solid melting at 52°–54° C. (Compound 1)

Calculated for $C_{11}H_{16}N_4O_2$: C, 55.93; H, 6.78; N, 23.73; Found: C, 55.56; H, 6.88; N, 23.55.

EXAMPLE 2

1-Diethanolaminomethylbenzimidazole

Using the general procedure of Example 1, but substituting for benzotriazole an equivalent amount of benzimidazole, the above named compound was obtained in a 72% yield as a solid melting at 90°–91° C. (Compound 2)

Calcd for $C_{12}H_{17}N_3O_2$: C, 61.28; H, 7.23; N, 17.87. Found: C, 61.24; H, 7.37; N, 17.60.

EXAMPLE 3

1-(N-Methylethanolaminomethyl)benzotriazole

Using the general procedure of Example 1, but replacing diethanolamine with an equivalent amount of N-methylethanolamine, the above-named compound was obtained in a 95% yield as a syrup. (Compound 3)

Calcd for $C_{10}H_{14}N_4O$: C, 58.25; H, 6.80; N, 27.18. Found: C, 58.20; H, 6.49; N, 27.98.

EXAMPLE 4

1-(N-Methylethanolaminomethyl)benzimidazole

Using the general procedure of Example 2, but replacing diethanolamine with an equivalent amount of N-methylethanolamine, the above-named compound was obtained in a 62% yield as a solid melting at 79°–80° C. (Compound 4)

Calcd for $C_{11}H_{15}N_3O$: C, 64.39; H, 7.32; N, 20.49. Found: C, 64.10; H, 7.42; N, 20.21.

EXAMPLE 5

1-Di-(2-propanol)aminomethylbenzotriazole

Using the general procedure of Example 1, but substituting for diethanolamine an equivalent amount of di-(2-propanol)amine, the above-named compound was obtained in a 70% yield as a solid melting at 71° C. (Compound 5)

Calcd for $C_{13}H_{20}N_4O_2$: C, 59.09; H, 7.58; N, 21.21. Found: C, 59.04; H, 7.79; N, 21.44.

EXAMPLE 6

1-(N-2-Hydroxyethylpiperazino)methylbenzotriazole

Using the general procedure of Example 1, but replacing diethanolamine with an equivalent amount of N-β-hydroxyethylpiperazine, the above-named compound was obtained in a yield of 43% as a solid melting at 81° C. (Compound 6)

Calcd for $C_{13}H_{19}N_5O$: C, 59.77; H, 7.28; N, 26.82. Found: C, 57.08; H, 7.21; N, 25.42.

In Examples 7–8, the compounds of the instant invention are Mannich bases derived from primary amines and have the general formula

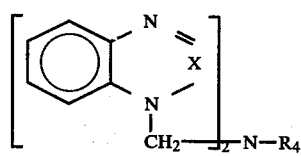

| Example | X | R₄ |
|---|---|---|
| 7 | N | —CH₂CH₂CH₂OCH₃ |
| 8 | CH | —CH₂CH₂CH₂OCH₃ |

EXAMPLE 7

N,N-Bis-(1-benzotriazolylmethyl)-3-methoxypropylamine

Using the general procedure of Example 1, but using only a half molar equivalent of 3-methoxypropylamine in place of diethanolamine, the above-named compound was obtained in a yield of 75% as a solid melting at 98°–100° C. after recrystallization from ethanol. (Compound 7)

Calcd for $C_{18}H_{21}N_7O$: C, 61.54; H, 5.98; N, 27.92. Found: C, 60.56; H, 5.99; N, 27.57.

EXAMPLE 8

N,N-Bis-(1-benzimidazolymethyl)-3-methoxypropylamine

Using the general procedure of Example 7, but replacing the benzotriazole with an equivalent amount of benzimidazole, the above-named compound was obtained in a yield of 68% as a solid melting at 120°–121° C. (Compound 8)

EXAMPLE 9

Testing of the Instant Compounds as Passivating Agents in a Water-Based Functional Fluid Specimens of metals typical of those which may be present in the cooling system of an internal combustion engine were totally immersed in an aerated test solution for two weeks at 82° C. The corrosion inhibiting properties of the solution were evaluated on the basis of weight losses incurred by the metal specimens.

The apparatus used is shown in the FIG. 1 and is as follows:

A 1000 ml "culture vessel" was fitted with a multi-socket flange lid (13) in one socket of which was placed a water-cooled, reflux condenser (16). In another socket of said lid was placed a gas distribution tube (not shown) with a sintered head of porosity grade No. 2. A flowmeter (not shown) suitable for controlling the aeration rate to 100±15 ml per minute was used. A cylinder of air (not shown) was attached to the flometer and the gas distribution tube. A thermometer (14) with a range of 5° to 105° C. adapted to fit another socket on the flange lid was inserted into the vessel.

The vessel was immersed into a water bath (not shown) capable of maintaining a temperature of 82°±2° C. A metal plate (not shown) was adapted to fit the water bath so that six culture vessels may be accommodated concomitantly if desired.

The metal specimens (50 mm×25 mm with a central 6 mm hole) were as follows:
(1) Steel
   U.S. SAE 1020 cold-rolled steel stock
(2) Copper
   Type ETP or STP of U.S. Standard specification for copper sheet, plate or rolled bar ASTM B 152, SAE 71 cold-rolled steel stock.
(3) Brass
   Alloy No. 8 of U.S. standard specification for brass plate, sheet, strip and rolled bar ASTM B 36, SAE 70C
(4) Solder
   Alloy grade 30A or 30B of U.S. ASTM B 32
(5) Cast Aluminum
   Alloy SC 64C of U.S. ASTM B 179, SAE 329
(6) Cast Iron
   Alloy No. 120 of U.S. ASTM 159, SAE 120

All metal specimens were vigorously scrubbed with pumice and a moist bristle brush, rinsed in cold water and then acetone, dried and weighed.

The specimens (1-6) were assembled on a brass machine screw (12) covered with thin walled insulating tubing of a diameter small enough to slip easily through the central hole in the specimens. They were separated from each other by cylindrical spacers (8-10) 5 mm. long, 11 mm. outside diameter, 6 mm. inside diameter. At each end of the assembly there was a brass "leg" (7) 50 mm. by 25 mm., cut from 1.5 mm. brass sheet and with a hole 6 mm. in diameter off center towards one end of the brass piece, oriented with their long axis in the same direction as the long axis of the specimen (see FIG. 1).

The specimens (1-6) and legs (7) were assembled in the following order (see FIG. 1)—Brass "leg" (7), copper (6), solder (5), brass (4), steel (3), cast iron (2), cast aluminum (1), brass "leg" (7). The spacers between the brass "legs" and the adjacent specimens and between the brass and steel specimens were of an insulating material (8), those between the brass, solder and copper specimens were of brass (10), and those between the steel, aluminum and iron specimens were of steel (9).

The assembly of "legs" spacers and specimens was tightened together by means of a brass nut (11) so as to ensure that the three specimens in each section were in good electrical contact with each other.

An antifreeze formulation was then made up as follows:

| | |
|---|---|
| monoethylene glycol | 92.8% by weight |
| triethanolamine | 2.9% by weight |
| phosphoric acid (s.g. 1.75) | 1.1% by weight |
| compound of Example 1 | 0.2% by weight |

-continued

| | |
|---|---|
| borax | 3.0% by weight |

250 ml of this antifreeze composition was diluted with 500 ml of water containing 0.444 g/l $Na_2SO_4$ and 0.165 g/l NaCl. and the solution (15) placed in the vessel as shown in FIG. 1. The vessel was immersed in a water bath at 82°±2° C., and the aeration rate was adjusted to 100±15 ml. per minute.

The test was continued for 336 hours (2 weeks). At the end of the test, the specimen assembly was removed and dismantled. The individual metal specimens were washed in running water while brushing to remove loosely-held corrosion products. More tenacious products were removed as follows.

Iron and Steel
The specimen was dipped for 1 minute in 50% HCl solution containing 1% hexamine.

Copper and Brass
The specimen was immersed in 30% solution of HCl for 30 seconds.

Aluminum
The specimen was dipped for 5 minutes in a solution containing 2% chromic acid and 5% $H_3PO_4$, which was maintained at 80° C.

Solder
The specimen was immersed in a boiling 1% acetic acid solution for 5 minutes.

Final cleaning of all specimens was carried out by scrubbing with a moist brush. After thoroughly cleaning, the specimens were rinsed in acetone, dried and weighed.

Specimens are said to have passed this test if the corrosion loss is lower than the following losses:

| | |
|---|---|
| Steel | 2.0 mg./sq. in |
| Cast Iron | 2.0 mg./sq. in |
| Solder | 4.0 mg./sq. in |
| Copper | 2.0 mg./sq. in |
| Brass | 2.0 mg./sq. in |
| Cast Aluminum | 7.0 mg./sq. in |

Comparative tests were run using, in place of the compound of Example 1, like amounts of benzotriazole or 5-methylbenzotriazole as the passivating agent. The results are given below:

| Active Ingredient | Weight Change of Metal Specimens (mg/sq in) | | | | | |
|---|---|---|---|---|---|---|
| | Copper | Brass | Solder | Steel | Aluminum | Cast Iron |
| Compound of Example 1 | −0.14 | −0.02 | +0.37 | −0.47 | −0.83 | −0.64 |
| Benzotriazole | −0.09 | −0.96 | −0.14 | −0.65 | −0.81 | −1.52 |
| 5-Methyl-benzotriazole | −0.07 | +0.14 | −0.09 | −0.63 | −1.84 | −2.44 |

EXAMPLE 10

When the test procedure of Example 9 was repeated using the compounds of Examples 5 or 6 in place of the compound of Example 1, comparable passivating activity was obtained in the antifreeze test systems.

What is claimed is:
1. A compound having the formula

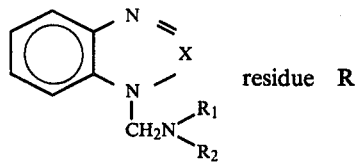

wherein
X is N or CR,
R is hydrogen or an alkyl of 1 to 4 carbon atoms,
$R_1$ and $R_2$ are the same or different and each is a residue of the formula
$R_3O[(alkylene)O]_x$alkylene,
$R_3$ is hydrogen or alkyl of 1 to 2 carbon atoms,
"alkylene" is a straight or branched chain alkylene of 2 to 3 carbon atoms,
x is 0, 1, 2, 3 or 4; or
$R_1$ is said residue and $R_2$ is hydrogen, alkyl of 1 to 4 carbon atoms, cyclohexyl, benzyl or a radical of the formula

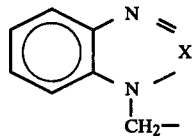

or $R_1$ and $R_2$ together are $$-CH_2CH_2NCH_2CH_2-\atop |\phantom{xx}CH_2CH_2OH}$$

2. A compound according to claim 1 wherein X is N or CR, R is hydrogen or methyl, $R_1$ and $R_2$ are the same or different and each is a residue of the formula $R_3O[(alkylene)O]_x$alkylene, $R_3$ is hydrogen or methyl, and x is 0; or $R_1$ is said residue and $R_2$ is hydrogen, methyl or the radical of the formula

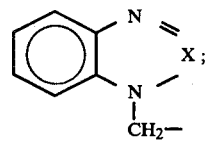

or $R_1$ and $R_2$ together are $$-CH_2CH_2NCH_2CH_2-.\atop |\phantom{xx}CH_2CH_2OH}$$

3. A compound according to claim 1 wherein X is N or CH.
4. A compound according to claim 3 wherein X is N.
5. A compound according to claim 1 wherein each of $R_1$ and $R_2$ is a residue of the formula $R_3O$ [(alkylene)O]$_x$ alkylene.
6. A compound according to claim 5 wherein $R_3$ is hydrogen and x is 0.
7. A compound according to claim 1 wherein $R_1$ and $R_2$ are the same or different and each is $R_3O[(alkylene)O]_x$alkylene; or $R_1$ is said residue and $R_2$ is hydrogen or methyl; $R_3$ is hydrogen or methyl; and x is 0.
8. A compound according to claim 1 which is 1-diethanolaminomethylbenzotriazole.
9. A compound according to claim 1 which is 1-diethanolaminomethylbenzimidazole.
10. A compound according to claim 1 which is 1-(N-methylethanolaminomethyl)benzotriazole.
11. A compound according to claim 1 which is 1-(N-methylethanolaminomethyl)benzimidazole.
12. A compound according to claim 1 which is 1-di-(2-propanol)aminomethylbenzotriazole.
13. A compound according to claim 1 which is 1-(N-2-hydroxyethylpiperazino)methylbenzotriazole.
14. A compound according to claim 1 which is N,N-bis-(1-benzotriazolymethyl)-3-methoxypropylamine.
15. A compound according to claim 1 which is N,N-bis-(1-benzimidazolymethyl)-3-methoxypropylamine.
16. A composition comprising
(a) a water-based functional fluid, and
(b) from 0.001 to 5% by weight based on the total composition of a compound according to claim 1, said compound acting as a metal passivator.
17. A composition according to claim 16 wherein the functional fluid is anti-freeze composition.
18. A composition according to claim 16 where in the metal passivator compound (b), each of $R_1$ and $R_2$ is a residue of the formula $R_3O[(alkylene)O]_x$alkylene, $R_3$ is hydrogen or alkyl of 1 to 2 carbon atoms and x is 0,1,2,3, or 4.
19. A composition according to claim 18 wherein $R_3$ is hydrogen and x is 0.
20. A composition according to claim 16 where in the metal passivator compound (b) $R_1$ and $R_2$ are the same or different and each is $R_3O[(alkylene)O]_x$alkylene or $R_1$ is said residue and $R_2$ is hydrogen or methyl; $R_3$ is hydrogen or methyl; and x is 0.
21. A composition according to claim 16 wherein the compound (b) is 1-diethanolaminomethylbenzotriazole.
22. A composition according to claim 16 wherein the functional fluid is an aqueous glycol system.
23. A composition according to claim 22 wherein the functional fluid is a hydraulic fluid.
24. A composition according to claim 16 wherein the functional fluid is a metal working fluid.

* * * * *

UNITED STATES PATENT AND TRADEMARK OFFICE
CERTIFICATE OF CORRECTION

PATENT NO. : 4,177,155
DATED : December 4, 1979
INVENTOR(S) : Alan F. Popplewell and David R. Clark It is certified that error appears in the above-identified patent and that said Letters Patent are hereby corrected as shown below:

Claim 1, Column 9, line 5, formula I:

" 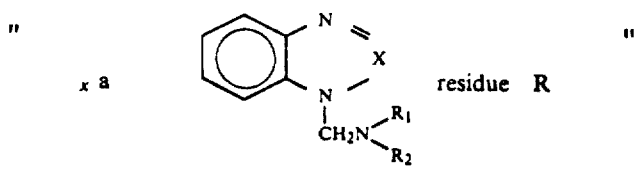 residue R "

should be -- 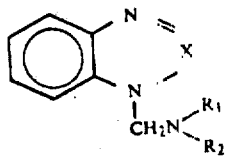 --.

Signed and Sealed this

Twelfth Day of August 1980

[SEAL]

Attest:

SIDNEY A. DIAMOND

Attesting Officer

Commissioner of Patents and Trademarks